(12) United States Patent
Kanazawa et al.

(10) Patent No.: US 11,619,624 B2
(45) Date of Patent: *Apr. 4, 2023

(54) HEALTH FACILITATION SYSTEM, SENSOR, AND HEALTH FACILITATION METHOD

(71) Applicant: FIRST SCREENING CO., LTD., Tokyo (JP)

(72) Inventors: Yohei Kanazawa, Tokyo (JP); Yoshito Tsunoda, Tokyo (JP)

(73) Assignee: FIRST SCREENING CO., LTD.

( * ) Notice: Subject to any disclaimer, the term of this patent is extended or adjusted under 35 U.S.C. 154(b) by 283 days.

This patent is subject to a terminal disclaimer.

(21) Appl. No.: 17/042,754

(22) PCT Filed: Mar. 30, 2018

(86) PCT No.: PCT/JP2018/013645
§ 371 (c)(1),
(2) Date: Jan. 14, 2021

(87) PCT Pub. No.: WO2019/187018
PCT Pub. Date: Oct. 3, 2019

(65) Prior Publication Data
US 2021/0132037 A1    May 6, 2021

(51) Int. Cl.
*G01N 33/487* (2006.01)
*A61B 5/00* (2006.01)
(Continued)

(52) U.S. Cl.
CPC ..... *G01N 33/48792* (2013.01); *A61B 5/0002* (2013.01); *A61B 5/207* (2013.01);
(Continued)

(58) Field of Classification Search
CPC ............ G01N 33/48792; G01N 33/493; A61B 5/0002; A61B 5/207; A61B 5/6808; G08B 5/223
(Continued)

(56) References Cited

U.S. PATENT DOCUMENTS

2009/0123335 A1    5/2009  Nakamura et al.
2014/0121487 A1*   5/2014  Faybishenko .......... G16H 40/63
                                                    600/365
(Continued)

FOREIGN PATENT DOCUMENTS

JP    2005-172493 A    6/2005
JP    2006-042670 A    2/2006
(Continued)

OTHER PUBLICATIONS

Decision of Refusal issued by the Japanese Patent Office for Application No. 2019-565355, dated Sep. 29, 2020 (6 pages).
(Continued)

*Primary Examiner* — Kerri L McNally
(74) *Attorney, Agent, or Firm* — Harness, Dickey & Pierce, P.L.C.

(57) ABSTRACT

The health support system according to a preferred embodiment includes a sensor that outputs an output signal corresponding to a specific component in urine, a transmitter connected to the sensor, and a user terminal carried by the user. The user terminal includes a storage unit that stores an identifier corresponding to the user, a wireless receiving unit that receives a wireless signal from the transmitter, an output unit that outputs the data to an analysis system that analyzes the health state of the user based on a specific component indicated by the data when the identifier indicated by the wireless signal matches the identifier stored in the storage unit, and an acquisition unit that acquires information corresponding to the results of the analysis of the analysis system.

23 Claims, 9 Drawing Sheets

(51) Int. Cl.
*A61B 5/20* (2006.01)
*G01N 33/493* (2006.01)
*G08B 5/22* (2006.01)

(52) U.S. Cl.
CPC ......... *A61B 5/6808* (2013.01); *G01N 33/493* (2013.01); *G08B 5/223* (2013.01)

(58) Field of Classification Search
USPC .................................................... 340/539.12
See application file for complete search history.

(56) References Cited

U.S. PATENT DOCUMENTS

| | | | |
|---|---|---|---|
| 2014/0176913 A1 | 6/2014 | Wu | |
| 2015/0319486 A1* | 11/2015 | Wang | H04M 1/72412 725/62 |
| 2015/0330958 A1* | 11/2015 | Carney | G01N 33/0073 73/23.34 |
| 2016/0120473 A1 | 5/2016 | Linton et al. | |
| 2016/0345877 A1 | 12/2016 | Takeuchi et al. | |
| 2018/0104114 A1* | 4/2018 | Pepin | G01N 27/048 |
| 2018/0325743 A1* | 11/2018 | Ho | A61F 13/42 |
| 2019/0017994 A1 | 1/2019 | Tsuruoka et al. | |
| 2019/0254582 A1* | 8/2019 | Wei | G16H 40/67 |

FOREIGN PATENT DOCUMENTS

| | | |
|---|---|---|
| JP | 2007-121060 A | 5/2007 |
| JP | 2008-206592 A | 9/2008 |
| JP | 2010-054379 A | 3/2010 |
| JP | 2012-105839 A | 6/2012 |
| JP | 2016-214733 A | 12/2016 |
| JP | 6100447 B1 | 3/2017 |
| WO | 2003-001423 A1 | 1/2003 |

OTHER PUBLICATIONS

International Search Report issued in PCT/JP2018/013645 (in English and Japanese), dated Jul. 3, 2018; ISA/JP.

International Search Report (English and Japanese) of the International Searching Authority issued in PCT/JP2019/042409, dated Jan. 21, 2020; ISA/JP (7 pages).

* cited by examiner

HEALTH FACILITATION SYSTEM, SENSOR, AND HEALTH FACILITATION METHOD

TECHNICAL FIELD

The present invention provides a technique for a system for health care support of a subject by use of body fluid measurement results of a body fluid of the subject.

BACKGROUND

Systems are known for monitoring a health of a subject by use of urine measurement results obtained from the urine of the user. For example, Patent Document 1 discloses a system for measuring an amount of urine by use of a sensor for measuring a weight of urine, the sensor being attached to a container (or a cup) for storing urine. Patent Document 2 discloses a system in which a urine sensor attached to a toilet bowl is used to measure components in the urine of a subject, and the results are used to assess disease of the subject.

PRIOR ART DOCUMENTS

Patent Document

[Patent Document 1] JP-A-2008-206592
[Patent Document 2] U.S. Pat. No. 6,100,447B

SUMMARY

Problem

According to Patent Document 1, it is necessary to store urine in a container, and thus a problem arises in that when handling the container urine may come into contact with a user's hand. Further, according to Patent Document 2, since it is necessary to attach a sensor to a toilet bowl, a problem arises in that a location where a user can measure urine is restricted.

In contrast, the present invention provides a technique for provision of a system for health care support of a subject by use of body fluid measurement results of a body fluid of the user, the system facilitating ease of handling, reducing restrictions on location of use, and obtaining accurate results.

Solution

According to one aspect of the invention, there is provided a health support system, including: a sensor that outputs an output signal corresponding to a specific component in urine; a transmitter connected to the sensor; a user terminal held by the user, wherein the transmitter includes, an input unit into which the output signal of the sensor is input, a storage unit that stores an identifier of the transmitter, a radio communicator that transmits a radio signal indicating data corresponding to the output signal and the identifier, the user terminal includes a storage unit that stores an identifier corresponding to the user, a wireless receiver that receives the radio signal from the transmitter, an output unit that outputs the data to an analysis system that analyzes a health condition of the user based on the specific component indicated by the data when the identifier indicated by the radio signal matches the identifier stored in the storage unit, an acquiring unit that acquires information corresponding to the results of the analysis from the analysis system.

The sensor may include a base, a sensor element attached to the base, and a detachable mechanism that detachably fixes the transmitter and includes a transmission path of the output signal of the sensor.

The sensor may include a sheet covering the sensor element, the base is made of a combustible material having a planar shape, and the sheet is made of paper softer than the base.

The sheet may include a thinner area than other areas, and the thinner area covers the sensor element with the sheet attached to the base.

The sheet may include a pocket, and the sensor element is housed in the pocket.

The base may include an adhesive layer for folding the base on the surface to which the sensor element is attached.

The health support system may include a protective film is adhered to the sheet at a position covering the adhesive layer on a surface of the sheet facing the base, when the sheet is attached to the base, the adhesive layer is not exposed, and when the sheet is peeled off from the base, the adhesive layer is exposed.

The base may be an undergarment or a diaper worn by a subject.

The sensor element may include a first sensor element that measures a first component in the urine, a second sensor element that measures a second component in the urine different from the first component.

The transmitter may include a first terminal into which the output signal of the first sensor element is input, a second terminal into which the output signal of the second sensor element is input, and a processor that processes in time division the signal input through the first terminal and the signal input through the second terminal.

The sensor may include a selector circuit that selects in time division the output signal of the second sensor element or of the first sensor element, an output terminal that outputs a signal showing the output signal of the first sensor element and the second sensor element selected in time division by the selector circuit.

The transmitter may be a wearable device worn on the user's body.

The wearable device may include an exposed contact on electrodes for obtaining electrical connections with the sensors.

The wearable device may include a transmission unit that performs non-contact signal transmission by electromagnetic induction with the sensor.

The storage unit may include a plurality of storage areas corresponding to each different identifier, the transmitter includes a receiving unit that receives designation of any of the plurality of storage areas, the storage unit stores data indicated by the output signal in one of the plurality of storage areas designated via the receiving unit, and the wireless communication unit transmits the wireless signal indicating the data stored in the designated one storage area and the identifier corresponding to the one storage area.

The health support system may include the analysis system, wherein the analysis system includes a storage unit that stores time series data indicating measurement results of the specific components in time series for each of a plurality of users, a generating unit that generates information related to the measurement results for the target user from among the plurality of users, using the time series data of the user, and an output unit that outputs the related information to a user terminal corresponding to the user.

The user terminal may include a receiving unit that receives input of information specifying food and drink consumed by the user, and the output unit outputs information on food and drink consumed by the user.

The generating unit may generate the related information in accordance with the information about the food and drink, and the data.

The generating unit may generate, as the related information, an image indicating a temporal change of a specific component in urine and a timing of ingestion of the food and drink.

The transmitter may include a power supply function to the sensor.

According to another aspect of the invention, there is provided a health support method using a health support system having a sensor that outputs an output signal corresponding to a specific component in urine, a transmitter connected to the sensor, and a user terminal carried by the user, the method comprising: transmitting, by the transmitter, data responsive to an output signal of the sensor and a radio signal indicative of the identifier of the transmitter; receiving, by the user terminal, the radio signal from the transmitter, outputting, by the user terminal, the data to an analysis system that analyzes the health condition of the user based on the specific component indicated by the data if the identifier indicated by the radio signal matches the identifier corresponding to the user, obtaining information corresponding to the results of the analysis from the analysis system.

According to yet another aspect of the invention, there is provided a sensor comprising: a base; a first wiring provided on the base; a second wiring provided on the base; a sensor element that outputs an output signal corresponding to a specific component in urine, the sensor element being connected to the first wiring and the second wiring, and a detachable mechanism connected to the first wiring and the second wiring, having a transmission path of an output signal transmitted through the first wiring and the second wiring, the detachable mechanism detachably fixing the transmitter that wirelessly transmits data indicating the output signal to another device.

The base may be an undergarment or a diaper worn by a subject.

According to yet another aspect of the invention, there is provided a health support system comprising: a sensor that outputs an output signal corresponding to a specific component in the urine, a transmitter connected to the sensor, wherein the transmitter includes an input unit into which the output signal of the sensor is input, a storage unit that stores an identifier of the transmitter, a wireless communication unit that transmits a wireless signal indicating data corresponding to the output signal and the identifier, to a user terminal owned by the user.

BRIEF DESCRIPTION OF REFERENCE NUMERALS

1: health support system, 10: urine sensor, 11: base, 12: sensor element, 13: detachment mechanism, 14: wiring, 15: sheet, 20: transmitter, 21: input unit, 22: signal processing unit, 23: storage unit, 24: wireless communication unit, 25: control unit, 26: power unit, 27: measurement unit, 30: user terminal, 31: storage unit, 32: wireless communication unit, 33: output unit, 34: acquisition unit, 35: communication unit, 36: control unit, 37: UI unit, 40: analysis system, 41: communication unit, 42: storage unit, 43: analysis unit, 44: generator, 45: output unit, 46: control unit, 131: Snap fit 131, 132: Snap fit, 151: pocket, 211: first terminal, 212: second terminal, 221: A/D conversion circuit, 222: selector circuit, 223: Memory controller, 231: RAM, 232: ROM, 241: chipset, 242: antenna, 251: processor, 261: power control circuitry, 262: battery, 301: CPU, 302: memory, 303: storage, 304: LTE chip, 305: Wi-Fi chip, 306: antenna, 307: touch screen, 308: speaker, 401: CPU, 402: memory, 403: storage, 404: NIC

DETAILED DESCRIPTION

1. Configuration

Figure 1:
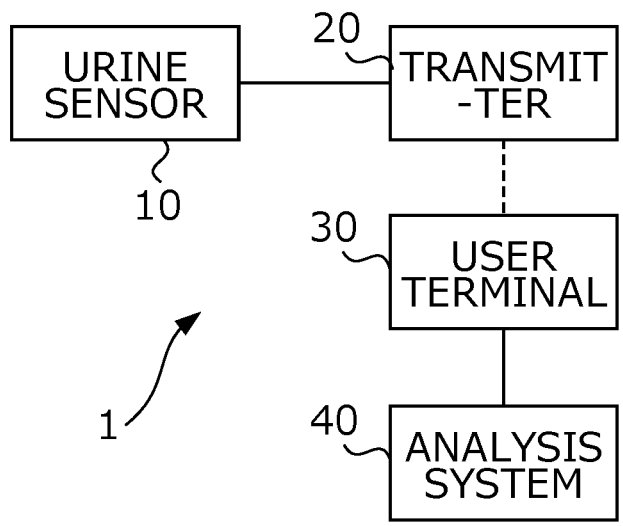
FIG. 1 shows an outline of a health support system 1 according to a first embodiment.

FIG. 1 shows an outline of a health support system 1 according to the first embodiment. The health support system 1 is a system that measures a specific component in the urine of a user and provides information for health support to the user using the measurement results. The health support system 1 includes a urine sensor 10, a transmitter 20, a user terminal 30, and an analysis system 40. The urine sensor 10 measures a specific component in urine. The transmitter 20 transmits the measurement results measured by the urine sensor 10 to the user terminal 30. The user terminal 30 receives the measurement results from the transmitter 20, and transmits the measurement results to the analysis system 40. The analysis system 40 analyzes the health condition of the user using the measurement results. The analysis system 40 transmits information corresponding to the analysis results to the user terminal 30. The user terminal 30 provides the user with information corresponding to the analysis results. In FIG. 1, one urine sensor 10, one transmitter 20, and one user terminal 30 are shown. However, the health support system 1 may have a plurality of one or more of these components.

1-1. Urine Sensor 10

Figure 2:
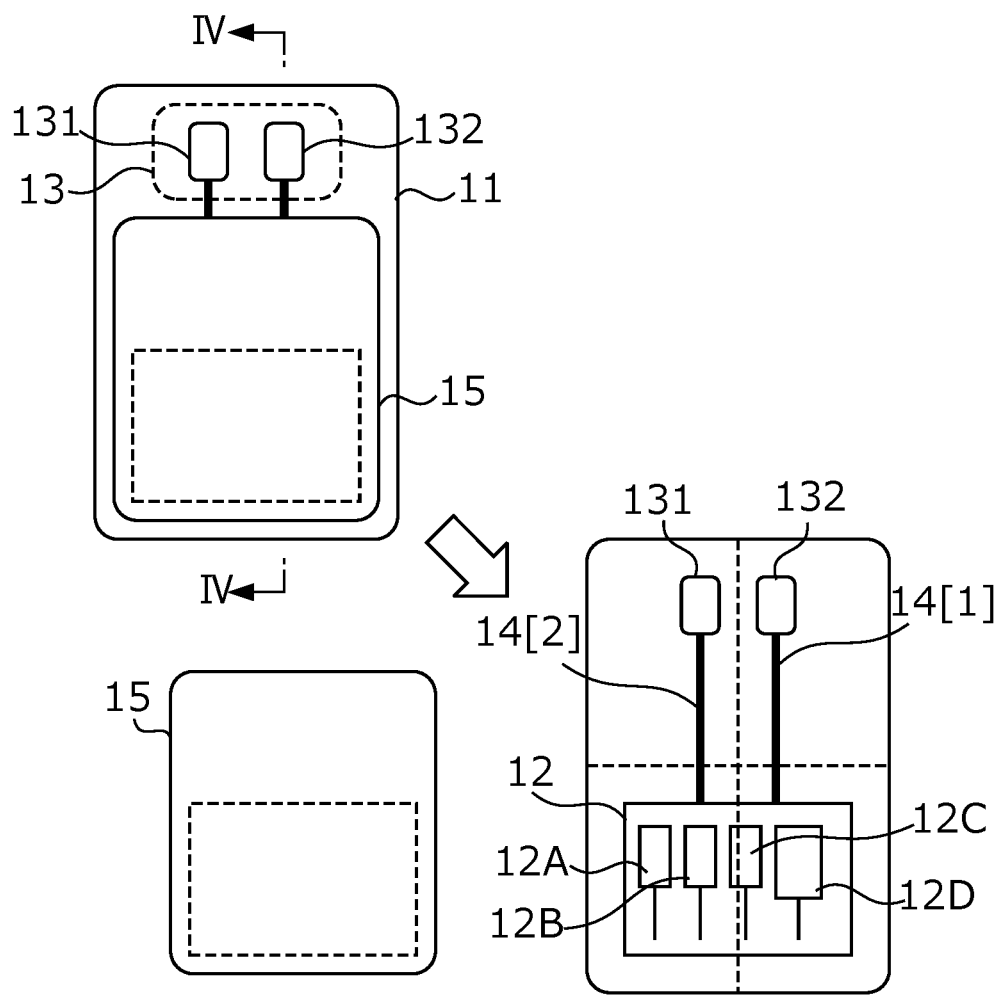
FIG. 2 shows an example of a configuration of a urine sensor 10.

FIG. 2 shows an example of the configuration of the urine sensor 10. In this example, the urine sensor 10 is used in combination with a paper used for wiping the penis or labia after the subject urinated. The urine sensor 10 includes a base 11, a sensor element 12, and a detachment mechanism 13. The base 11 is a member of the urine sensor 10, and is mechanically strong and of a size that is easy to handle. The sensor element 12 outputs a signal corresponding to a specific component in urine. As the sensor element 12, for example, a biosensor using an enzyme or a sensor using a diamond electrode is used. As the biosensor using enzymes, for example, the sensor described in an article by Nakamura et al. (Hideaki Nakamura, Yosuke Tsuboi and Masao Gotoh, "A simple potentiometric urine glucose biosensor using a paper-based disposable reagent sheet and a mobile pH meter," Current Topics in Analytical Chemistry, 9, pp. 71-75 (2012)) can be used. Sensors with diamond electrodes disclosed in, for example, Ogata et al. (G. Ogata, Y. Ishii, K. Asai, Y. Sano, F. Nin, T. Yoshida, T. Higuchi, S. Sawamura, T. Hori, K. Maeda, S. Komune, K. Doi, M. Takai, I. Findlay, H. Kusuhara, Y. Einaga, H. Hibino, "A microsensing system for the in vivo real-time measurement of local drug kinetics), Nature Biomed. Eng., 1, 654-666 (2017) can be used for urine sensor 10.

The sensor element 12 is attached to the base 11. In this example, plural sensor elements 12 are attached to base 11. The plural sensor elements 12 are each responsive to a different component in the urine. In one example, the urine sensor 10 has four sensor elements 12A, 12B, 12C, and 12D. The sensor element 12A (an example of the first sensor element) measures the pH of urine, the sensor element 12B (an example of the second sensor element) measures the uric acid value in urine, the sensor element 12C measures the oxalic acid value in urine, and the sensor element 12D measures the urinary glucose value in urine. The pH represents a concentration of hydrogen ions (an example of the first component) in urine, and thus can be considered to represent the measurement results of "a specific component in urine." Uric acid is an example of a second component in urine.

The detachment mechanism 13 is a mechanism for detachably fixing the base 11 to the transmitter 20. Detachable mechanism 13 forms a transmission path for transmitting the output signal from the sensor element 12. Detachable mechanism 13 is at least partially made of a conductive material, through which conductive material the output signal is transmitted.

In this example, the base 11 has a planar shape and is made of a combustible material. As a combustible material, cloth or paper is used, for example. A snap fit 131 and a snap fit 132 are formed on the base 11. The snap fit 131 and the snap fit 132 are examples of detachment mechanism 13. A wiring 14 is formed on the base 11. The wiring 14 is a wiring for transmitting the output signal of the sensor element 12 to the detachable mechanism 13 (snap fit 131 and snap fit 132). For one sensor element 12, one set of wirings (two wirings) 14 is used. When distinguishing these two wires, they are referred to as wiring 14[1] and wiring 14[2]. The wiring 14[1] and the wiring 14[2] are examples of the first wiring and the second wiring, respectively. The sensor element 12 is connected to the wiring 14[1] and the wiring 14[2] and outputs an output signal corresponding to a specific component in the urine. If the urine sensor 10 has k sensor elements 12, where k is a natural number greater than or equal to 2, then k sets of wirings 14 are used. If signals from k sensor elements 12 are output in spatial division, the detachable mechanism 13 has, for example, two wirings 14 and two snap-fits. In order to simplify the drawings, only two wirings 14 and two snap fits are shown in this figure. The urine sensor 10 further includes a sheet 15 covering the sensor element 12. The sheet 15 is made of a material softer than the base 11, specifically, a material having a stiffness lower than that of the base 11.

Figure 3:
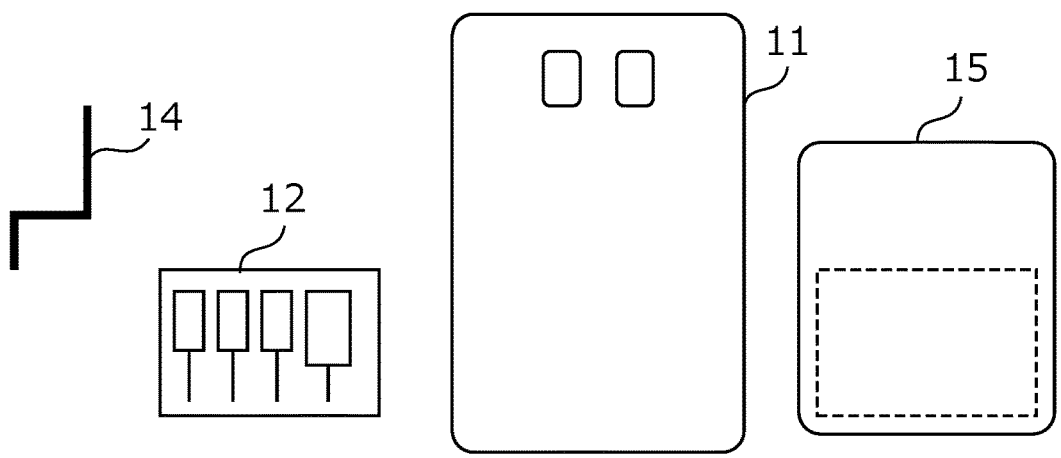
FIG. 3 shows an exploded view of the urine sensor 10.

FIG. 3 shows an exploded view of the urine sensor 10. The urine sensor 10 is formed from a base 11 including a detachment mechanism 13, a sensor element 12, a wiring 14, and a sheet 15. In this example, urine sensor 10 is disposable. Following urination, the user wipes urine from the penis with the surface of the urine sensor 10 covered with the sheet 15. The urine passes through the sheet 15 and reaches the sensor element 12. The sensor element 12 measures a specific component in the urine. After measurement, the user peels the sheet 15 from the base 11 and flushes the sheet 15 down the toilet. The user folds the base 11 and disposes of it in a trash bin. An adhesive layer 111 for folding the base 11 is formed on the back surface of the base 11 to which the sensor element 12 is attached. On a surface of the sheet 15 facing the base 11, a protective film 153 is adhered to a region that is in contact with the adhesive layer 111 in a state in which the sheet 15 is attached to the base 11, and the adhesive layer 111 is covered with the protective film 153 and is not exposed on the surface. When the sheet 15 is peeled from the base 11, the protective film 153 peels off from the adhesive layer 111, and the adhesive layer 111 is exposed. It is of note that this is an example of a disposal method, and actually, the urine sensor 10 is disposed of in accordance with local laws and the like in the locality in which it is used.

Figure 4:
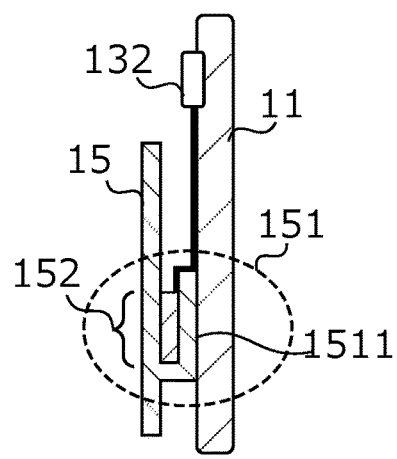
FIG. 4 illustrates a cross-sectional structure of a urine sensor 10.

FIG. 4 illustrates a cross-sectional structure of the urine sensor 10. FIG. 4 shows a cross section of the urine sensor 10 through the center of the base 11 when the base 11 is viewed from the front, which is a IV-IV cross section in FIG. 2. In this example, the sheet 15 has a pocket 151 on the surface facing the base 11. The sensor element 12 is housed in a pocket 151. The surface 1151 of the pocket 151 on the side of the base 11 is adhered to the base 11 by, for example, an adhesive. The area 152 of the sheet 15 that covers the sensor element 12 is thinner than other areas, which is an example of a thinner portion. This is to make it easier for urine to reach the sensor element 12. The sheet 15 is perforated around the pocket 151 so that portions other than the pocket 151 can be separated and disposed of.

In this example, the urine sensor 10 itself does not have a power source (or a battery) and operates by receiving power from another device (transmitter 20 in this example).

Figure 5:
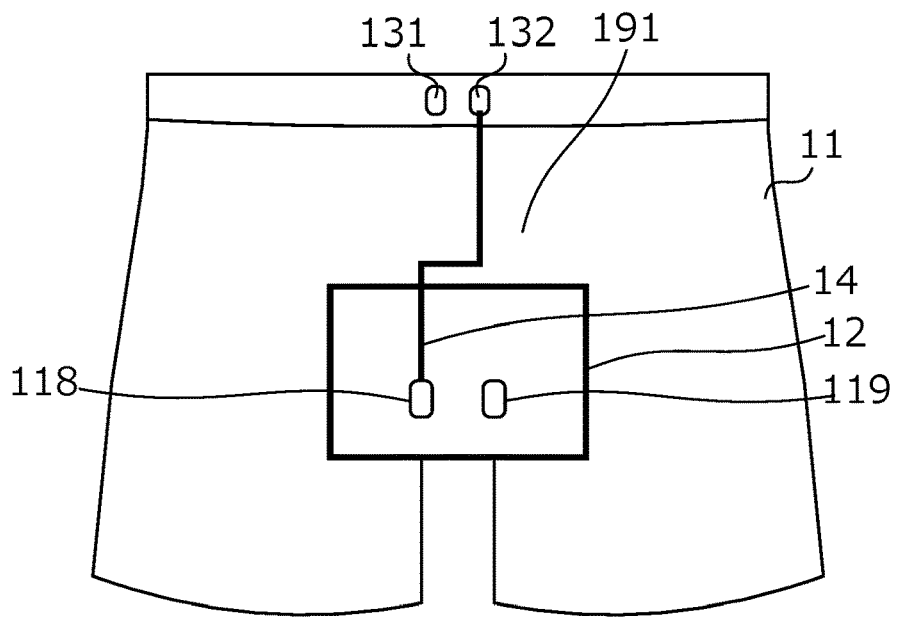
FIG. 5 illustrating another example of a configuration of a urine sensor 10.

FIG. 5 shows another exemplary configuration of the urine sensor 10. The urine sensor 10 illustrated in FIGS. 2-4 is intended to be held by a user with his/her hand and wipe away residual urine. In the example shown in FIG. 5, the base 11 is in a form of an undergarment (in particular, a male undergarment). In the base member 11, the sensor element 12 is attached at a position corresponding to the crotch. In this example, only the sensor element 12 is disposable and the base 11 is repeatedly used. For use in the urine sensor 10, a replacement sensor element 12 is sold. An adhesive layer is provided on the back surface of the sensor element 12. The adhesive layer is sold, for example, in a state of being covered with a protective film. The user wears an undergarment, which is the base 11. The user prepares the sensor element 12 before urination and attaches it to the base 11. After urination, the user pierces the base 11 to which the sensor element 12 is attached. When the base 11 is pierced, the residual urine contacts the sensor element 12, and the sensor element 12 outputs a signal indicating the measurement results of the specific component.

1-2. Transmitter 20

Figure 6:
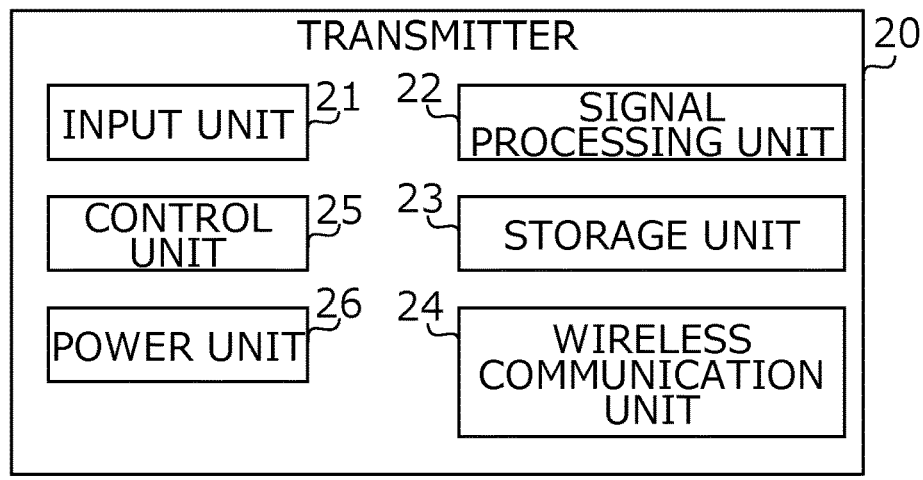
FIG. 6 illustrating a configuration of a transmitter 20.

FIG. 6 illustrates a functional configuration of the transmitter 20. The transmitter 20 is a device for transmitting information measured by the urine sensor 10 to the user terminal 30. While the urine sensor 10 is disposable, the transmitter 20 is used repeatedly.

Transmitter 20 has an input unit 21, a signal processing unit 22, a storage unit 23, a wireless communication unit 24, a control unit 25, and a power supply unit 26. The input unit 21 receives an input of an output signal from the urine sensor 10. The signal processing unit 22 performs various signal processing. The processing performed by the signal processing unit 22 includes, for example, a process of storing the signal received by the input unit 21 in the storage unit 23 as data. Storage unit 23 stores various data. The wireless communication unit 24 performs wireless communication with another device in accordance with a predetermined communication standard. This communication standard is, for example, IEEE 802 15.1, i.e., Bluetooth (registered trademark). The control unit 25 controls other elements of the transmitter 20. The power supply unit 26 is an example of a power supply unit for supplying power used for the operation of the transmitter 20 and the urine sensor 10.

Figure 7:
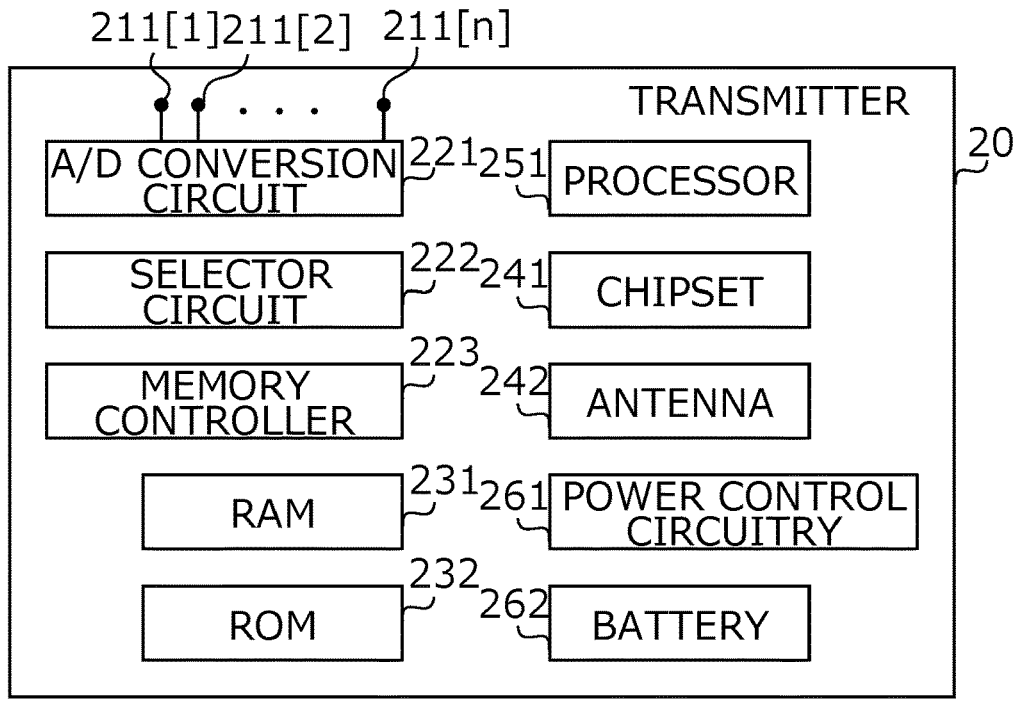
FIG. 7 illustrating a hardware configuration of a transmitter 20.

FIG. 7 illustrates a hardware configuration of the transmitter 20. Transmitter 20 has n input terminals (including the first terminal 211[1] and second terminal 211[2]), A/D converter circuit 221, selector circuit 222, memory controller 223, RAM 231, ROM 232, chip set 241, antenna 242, processor 251, a power control circuit 261, and a battery 262. The n input terminals (n≥2) including the first terminal 211[1], the second terminal 211[2] . . . and the n-th terminal 211[$n$] are terminals corresponding to a case where the urine sensor 10 has a plurality of sensor elements 12. The transmitter 20 corresponds to a urine sensor 10 having a maximum of n sensor elements 12. The signal input via the k-th terminal 211[$k$] is referred to as a signal S[k]. k is a natural number that satisfies 1≤k≤n. A/D converter circuit 221 converts the signal input via the input terminals (analog signal) to a digital signal. Selector circuit 222 selects one signal from the n input signals, and outputs the selected signal. In this example, the selector circuit 222 repeatedly selects in turn one signal from the n input signals. Specifically, after the signals S[1] to S[n] are selected in turn as signals S[1], S[2] to S[n], the signals S[1] to S[n] are again selected in turn. The selector circuit 222 selects the S[n] from the signal S[1] in time division. The memory controller 223 writes data into RAM 231 in accordance with the signals outputted from the selector circuits 222. Data obtained by converting an output signal from the urine sensor 10 is referred to as measurement data.

Figure 8:
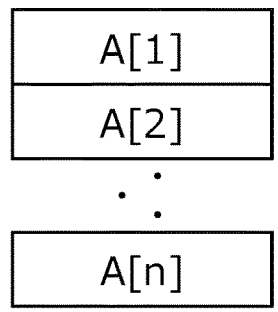
FIG. 8 illustrates a storage area of the measurement data.

FIG. 8 illustrates a storage area of measurement data. In RAM 231, the storage area of the measured data is divided into n segments (storage area A[1] to A[n]). The number of segments of the storage area is equal to the number of input terminals (the number of the largest sensor elements 12 that can be supported). The storage area A[k] stores data of the signal S[k] Each storage area stores the latest one measurement data.

Referring to FIG. 7 again. RAM 231 is a volatile storage device that stores measured data and other data. ROM 232 is a non-volatile storage device that stores a program or the like for execution by the processor 251. In this example, ROM 232 stores data-indicating identifiers that identify each of the plurality of transmitters 20. Hereinafter, this data is referred to as "identifier data"; and the identifier of the transmitter 20 is referred to as "transmitter identifier." This identifier allows each transmitter 20 to be distinguished from others even when multiple transmitters 20 are used in health support system 1. Chipset 241 and antenna 242 are respectively circuit groups and antennas for wireless communication in accordance with the communication standards described above. The processor 251 is a microcontroller for controlling the other elements of the transmitter 20. The battery 262 is a battery for supplying electric power for driving the transmitter 20 and the urine sensor 10, and may be a primary battery or a secondary battery. Power control circuit 261 is a circuit for controlling on-off of the power supply of the transmitter 20.

In this embodiment, the processor 251 sequentially specifies one storage area from among a plurality of storage areas of the measurement data in RAM 231, and reads the measured data from the designated storage area. The processor 251 adds an identifier of the storage area to the measurement data. As described with reference to FIG. 8, since the storage area and the sensor element 12 have a one-to-one correspondence, the identifier of the storage area corresponds to the identifier of the sensor element 12, which will be described later. Processor 251 controls chipset 241 to transmit a pair of measurement data and storage area identifiers.

With respect to the relationship between FIG. 5 and FIG. 6, the first terminal 211 and the second terminal 212 is an example of the input unit 21. A/D conversion circuit 221, the selector circuit 222, and the memory controller 223 is an example of the signal processing unit 22. RAM 231 and ROM 232 are examples of the storage unit 23. Chipset 241 and antenna 242 are examples of the wireless communication unit 24. The processor 251 is an example of the control unit 25. Power control circuit 261 and the battery 262 are examples of the power supply unit 26.

Figure 9:
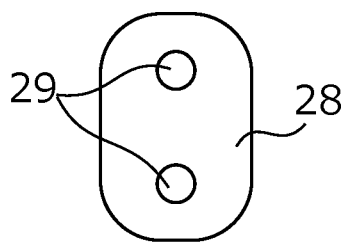
FIG. 9 illustrates an external appearance of a transmitter 20.

FIG. 9 illustrates an appearance of the transmitter 20. In this example, the transmitter 20 has a housing 28 and a detachment mechanism 29. The housing 28 is a housing for protecting elements such as the processor 251 and for facilitating handling. The housing 28 may have a structure in which at least a part thereof can be opened and closed so that the battery 262 can be replaced. The detachment mechanism 29 is a mechanism for detaching the urine sensor 10 from the detachment mechanism 13, and is, for example, a snap fit.

1-3. User Terminal 30

Figure 10:
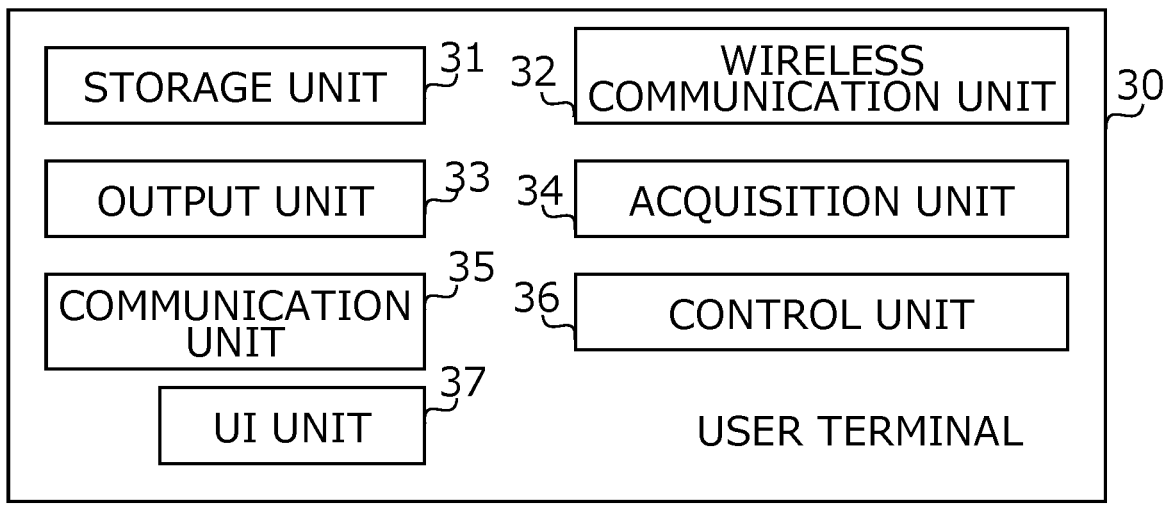
FIG. 10 illustrates a functional configuration of the user terminal 30.

FIG. 10 illustrates a functional configuration of the user terminal 30. The user terminal 30 receives measurement data from the transmitter 20, and further displays information obtained by analyzing the measurement data. The user terminal 30 is carried by a user of the urine sensor 10.

The user terminal 30 includes a storage unit 31, a wireless communication unit 32, an output unit 33, an acquisition unit 34, a communication unit 35, a control unit 36, and a UI unit 37. The storage unit 31 stores various data. The data stored in the storage unit 31 includes an identifier (hereinafter, referred to as "user identifier") that specifies a user of the user terminal 30. Further, the data stored in the storage unit 31 includes information for specifying a pair of a user identifier and a transmitter identifier. In the present embodiment, the transmitter 20 is not shared by an unspecified number of users, but rather is used by either a single user of or a small number of users. The number of users using a certain transmitter 20 is limited. The user acquires the transmitter identifier of the transmitter 20 used by the user by one of several available methods, and stores the transmitter identifier in the storage unit 31 in association with the user identifier of the user.

The wireless communication unit 32 is an example of a wireless receiving unit that receives a wireless signal from the transmitter 20. The wireless communication unit 32 complies with the same communication standard (e.g., Bluetooth (registered trademark)) as the wireless communication unit 24 of the transmitter 20. When the identifier indicated by the received wireless signal and the identifier stored in the storage unit 31 conform, that is, when the sender identifier received from the sender 20 and the sender identifier stored in association with the user identifier in the storage unit 31 are identical, the output unit 33 outputs the measurement data received from the sender 20 to the analysis system 40. Match of the transmitter identifiers is confirmed here to exclude data transmitted from the transmitter 20 used by other users. When the transmitter identifier received from the transmitter 20 does not match the transmitter identifier stored in the storage unit 31 in association with the user identifier, the control unit 36 may delete the measurement data from the storage unit 31. The acquisition unit 34 acquires information corresponding to the results of analysis using the measurement data from the analysis system 40. The information corresponding to the analysis results may be information that indicates the analysis results of the measurement data, or may be information that is obtained from the analysis results.

The communication unit 35 performs communication according to a predetermined communication standard. The communication standard followed by the communication unit 35 differs from that of the wireless communication unit 32, and may be a mobile communication standard such as LTE (Long Term Evolution) or a wireless LAN standard such as Wi-Fi, for example. The control unit 36 controls other elements of the user terminal 30. The UI unit 37 provides a UI for the user of the user terminal 30. The UI unit 37 acts as a receiving unit that receives an input of an instruction or information from a user, and an output unit that outputs various types of information to the user. The output unit includes a display unit for visually outputting various types of information.

Figure 11:
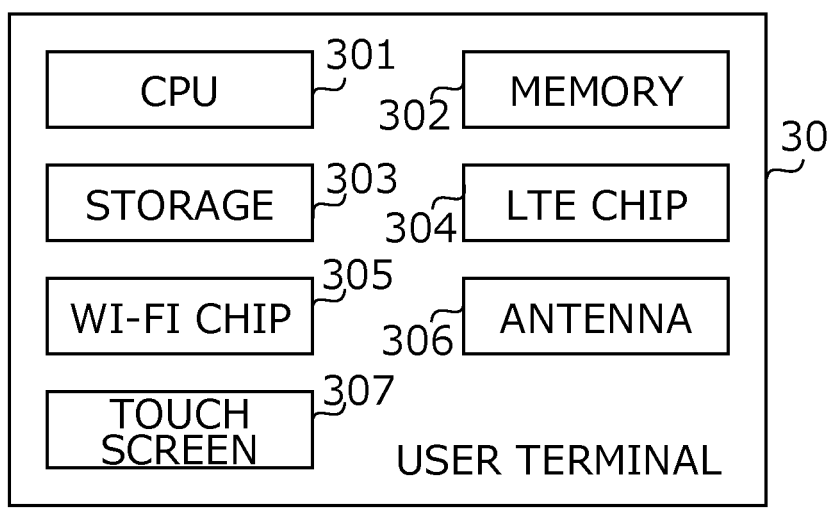
FIG. 11 illustrates a hardware configuration of the user terminal 30.

FIG. 11 illustrates a hardware configuration of the user terminal 30. The user terminal 30 is a computer device, e.g., a smart phone, having a CPU 301, a memory 302, a storage 303, an LTE chip 304, a Wi-Fi chip 305, an antenna 306, a touch screen 307, and a speaker 308. The CPU 301 is a device that performs various operations according to a program and controls other hardware elements. The memory 302 is a main storage device that stores various data. The storage 303 is an auxiliary storage device that stores various data and programs. The LTE chip 304 is a chipset for communication in accordance with the LTE standard. The Wi-Fi chip 305 is a chip set for communication in accordance with Wi-Fi standard. The antenna 306, the LTE chip 304, and the Wi-Fi chip 305 is an antenna that transmits and receives radio waves. The touch screen 307 is an input/output device that has a display for displaying information, and a touch sensor is provided on a screen of the display device. The speaker 308 is an output device that outputs sound.

In this example, the storage 303 stores a program (hereinafter, referred to as "client program") that causes the computer device to function as the user terminal 30. When the CPU 301 executes the client program, the functions shown in FIG. 10 are implemented in a computer device.

The memory 302 and the storage 303 are examples of the storage unit 31 that is used when the CPU 301 executes the client program. The combination of the Wi-Fi chip 305 and the antenna 306 is an example of the wireless communication unit 32. The CPU 301 is an example of the output unit 33, the acquiring unit 34, and the control unit 36. The LTE chip 304 and the antenna 306 is an example of the communication unit 35.

1-4. Analysis System 40

Figure 12:
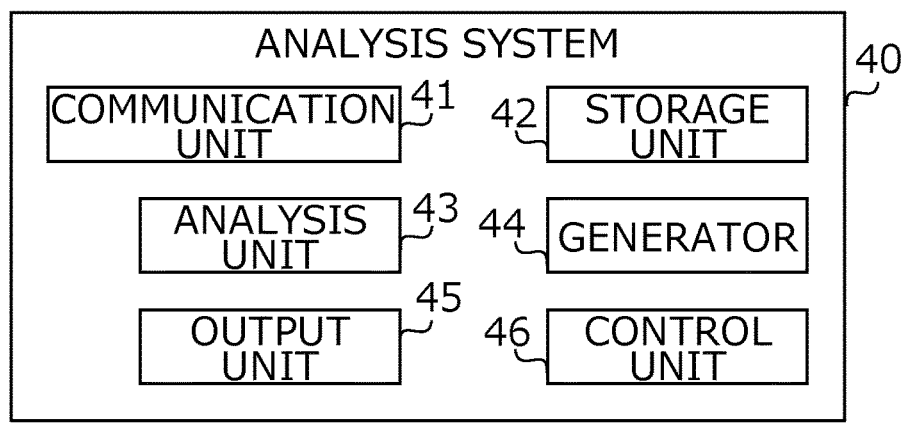
FIG. 12 illustrates a functional configuration of an analysis system 40.

FIG. 12 illustrates a functional configuration of the analysis system 40. The analysis system 40 analyzes the health state of the user using the measurement data output from the user terminal 30. The analysis system 40 may be implemented physically separate from the user terminal 30, such as in a cloud computing system, or may be implemented in the user terminal 30. By implementing the analysis system 40 in a cloud computing system, for example, a reduction in load on the user terminal 30 while performing statistical processing of measurement data for a plurality of users can be achieved. By implementing the analysis system 40 in the same device as the user terminal 30, the user terminal 30 can be used as a stand-alone device, and privacy of the measurement data can be maintained. In this example case the analysis system 40 is utilized in a cloud computing system.

Analysis system 40 includes a communication unit 41, a storage unit 42, an analysis unit 43, a generator 44, an output unit 45, and a control unit 46. The communication unit 41 communicates with the user terminal 30. The storage unit 42 stores various data. In this example, the data stored in the storage unit 42 includes data in which the measurement results (measurement data) of the specific component in the urine is recorded in time series (hereinafter referred to as "time series data"). The storage unit 42 stores the time series data for each of the plurality of users. The analyzing unit 43 analyzes the health state of the user using the time series data. The analysis of the health state is performed in accordance with a predetermined algorithm. AI (Artificial Intelligence) techniques such as deep learning may be used for analysis of health conditions. The generation unit 44 generates information related to the analysis results in the analysis unit 43. The related information includes, for example, at least one of the following (1) to (4).

(1) Information directly indicating the analysis results (e.g., visualizing of time-series data as a graph).

(2) Information obtained by interpretation of the analysis results (e.g., information for presenting disease names inferred from time-series data).

(3) Advice based on the results of the analysis (e.g., a diet menu or exercise menu appropriate for a user analyzed as likely having diabetes).

(4) Recommendations for commodities associated with analysis results (e.g., recommendations for beverages using green leafy vegetables (e.g., kale) for users with low pH (acidic).

The above-mentioned related information is an example of information corresponding to the analysis results of the measurement data. The output unit 45 outputs data that indicates the related information (hereinafter referred to as "related information data") to the user terminal 30. The control unit 46 performs various controls.

Figure 13:
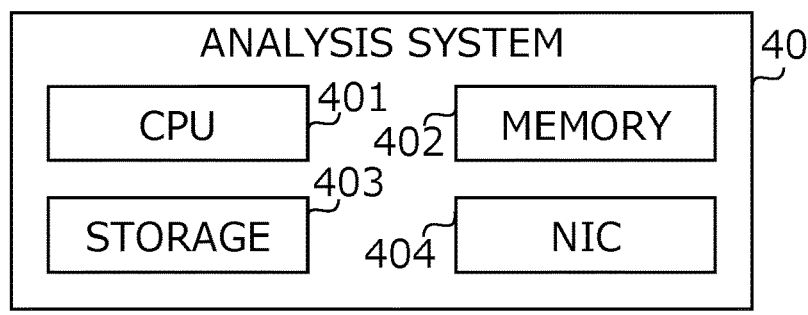
FIG. 13 illustrates a hardware configuration of an analysis system 40.

FIG. 13 illustrates an exemplary hardware configuration of the analysis system 40. The analysis system 40 is a computer device having a CPU 401, a memory 402, a storage 403, and a NIC (Network Interface Controller) 404, such as a server device on the Internet. The CPU 401 is a device that performs various operations in accordance with a program and controls other hardware elements. The memory 402 is a main storage device that stores various data. The storage 403 is an auxiliary storage device that stores various data and programs. The NIC 404 is a device that performs communication in accordance with a predetermined communication standard (e.g., Ethernet).

In this example, the storage 403 stores a program (hereinafter, referred to as an "analysis program") that causes a computer device to act as the analysis system 40. The NIC 404 is an example of the communication unit 41 upon execution of the CPU 401 of the analysis program. The memory 402 and the storage 403 are examples of a storage unit 42. The CPU 401 is an example of the analyzing unit 43, the generating unit 44, the outputting unit 45, and the control unit 46.

2. Operation

Figure 14:
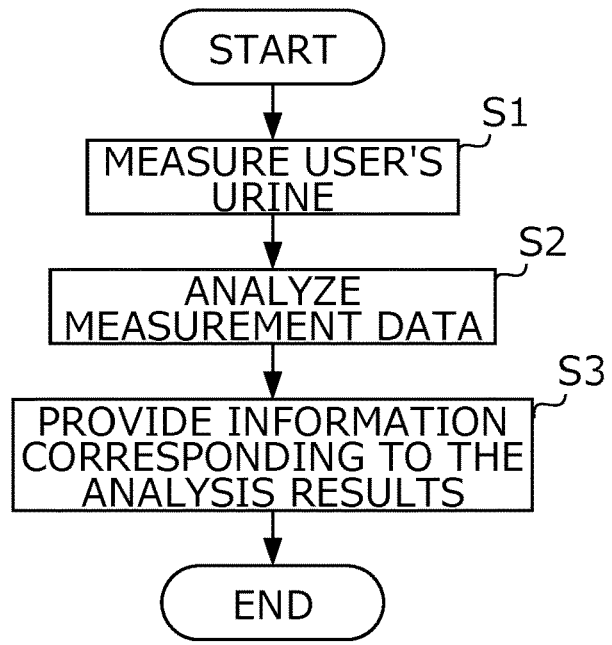
FIG. 14 illustrates an outline of an operation of a health support system.

FIG. 14 illustrates an outline of the operation of the health support system 1. At step S1, the health support system 1 measures the user's urine. At step S2, the health support system 1 analyzes the measurement data. At step S3, the health support system 1 provides information corresponding to the analysis results of the measurement data to the user.

2-1. Measurement

Figure 15:
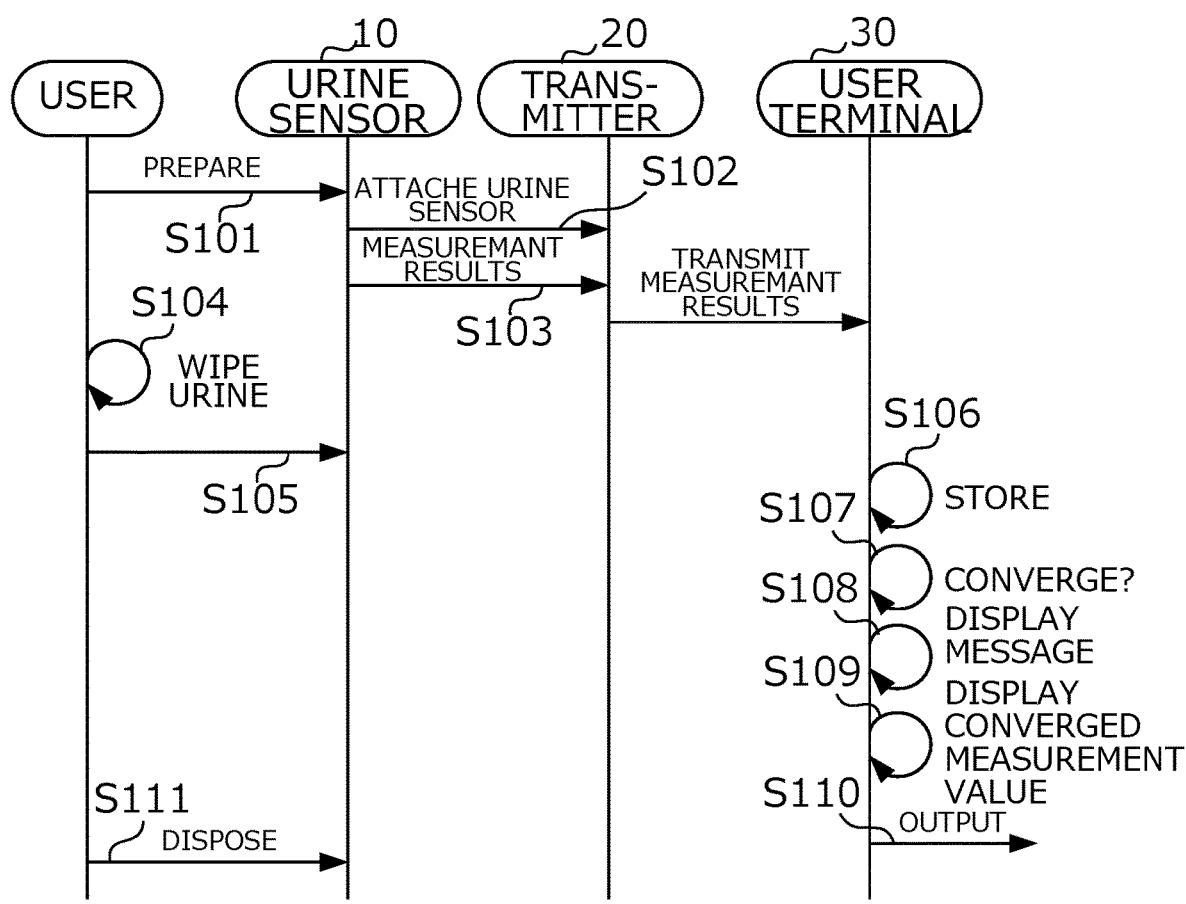
FIG. 15 shows a sequence chart illustrating details of the measurement process.

FIG. 15 is a sequence chart illustrating details of the measurement process. Here, an example is described in which the urine sensor 10 of FIG. 2 is used. The transmitter 20 and the user terminal 30 communicate using Bluetooth (registered trademark). Pairing between the transmitter 20 and the user terminal 30 is completed in accordance with a predetermined procedure prior to the sequence shown in FIG. 15. In this example, the transmitter 20 is continuously powered on, and the transmitter 20 and user terminal 30 are continuously paired via Bluetooth. The transmitter 20 and the user terminal 30 need not always be connected, and may be disconnected when a sleep mode or the like is implemented.

At step S101, the user prepares the urine sensors 10. The urine sensor 10 may be sold as a separate package. A protective film is attached to the sensor element 12. The user opens the package of the urine sensor 10 and removes the protective film from the sensor element 12. At step S102, the user attaches the urine sensor 10 to the transmitter 20. When the urine sensor 10 is attached to the transmitter 20, power is supplied from the transmitter 20 to the urine sensor 10. Upon supply of power, the urine sensor 10 outputs (at step S103) signals indicative of the results of the measurements. The urine sensor 10 continuously outputs a signal while power is supplied. The transmitter 20 continues to transmit measurement data to the user terminal 30 at regular time intervals while a pairing connection is established with the user terminal 30. The user terminal 30 continuously receives measurement data from the transmitter 20 via this connection.

At step S104, the user urinates. In step S105, the user wipes a penis or labia (i.e., wipes urine) with the surface of the urine sensor 10 to which the sheet 15 is attached. Upon exposure to urine, the sensor element 12 reacts with the urine, and the output signal, e.g., the voltage value changes.

Figure 16:
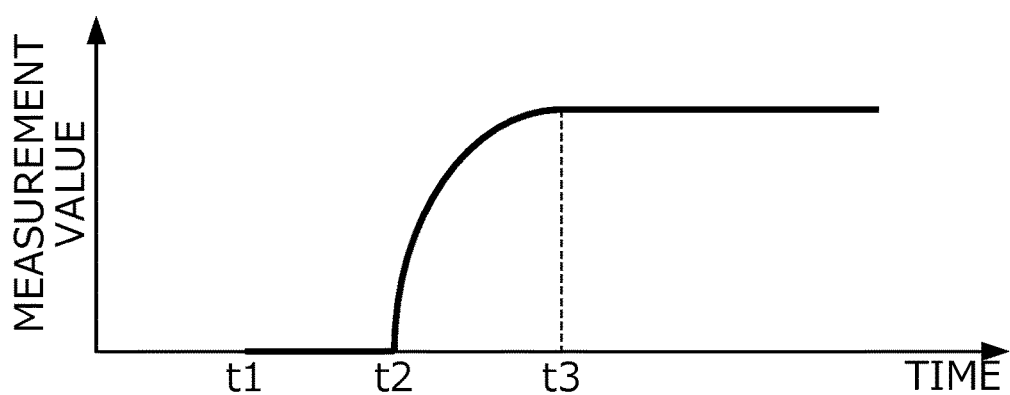
FIG. 16 illustrates the time variation of the measured value.

FIG. 16 illustrates a temporal change in a measured value. The horizontal axis represents time, and the vertical axis represents measured values, for example, a concentration of a specific component in urine. When the urine sensor 10 is not attached, the input terminal of the input unit 21 is open, and thus a voltage value is not measured and a measured value is not obtained. At time t1, the urine sensor 10 is attached to the transmitter 20 and measurements begin to be obtained. At this point, however, the sensor element 12 is not in contact with the urine, and thus the measurement is essentially zero. At time t2, the user wipes the urine, and the urine and the sensor element 12 start to react. The reaction proceeds with a certain time constant and finally converges.

Referring once more to FIG. 15; at step S106, the user terminal 30 stores the measured data received from the transmitter 20 in the storage unit 31. The control unit 36 determines (at step S107) whether the measured value indicated by the measured data satisfies a predetermined convergence condition. When it is determined that the convergence condition is satisfied, the UI unit 37 displays (at step S108) a message indicating, for example, a successful measurement. The output unit 33 adds attribute data to the measurement data indicating the converged measurement value. The attribute data is data that indicates the attributes of the measurement value; and in this example includes a time stamp that indicates the measured time and a user identifier that identifies the user subject to measurement. The storage unit 31 stores the measurement data that indicates the converged measurement data at step S109. The output unit 33 outputs (at step S110) the measured data to the analysis system 40.

When the measurement data is output to the analysis system 40, the UI unit 37 displays a message prompting the user to dispose of the urine sensor 10. At this time, the UI unit 37 may reproduce a moving image explaining how to dispose of the urine sensor 10. The user removes the urine sensor 10 from the transmitter 20. The user then peels the sheet 15 from the base 11 and flushes it down the toilet. The user folds and disposes (at step S111) the base 11 from which the sheets 15 have been peeled.

According to the present embodiment, urine measurement can be performed by the user wiping urine, and the results can be recorded. The urine sensor 10 is disposable and easy to handle for the user.

2-2. Analysis

Figure 17:
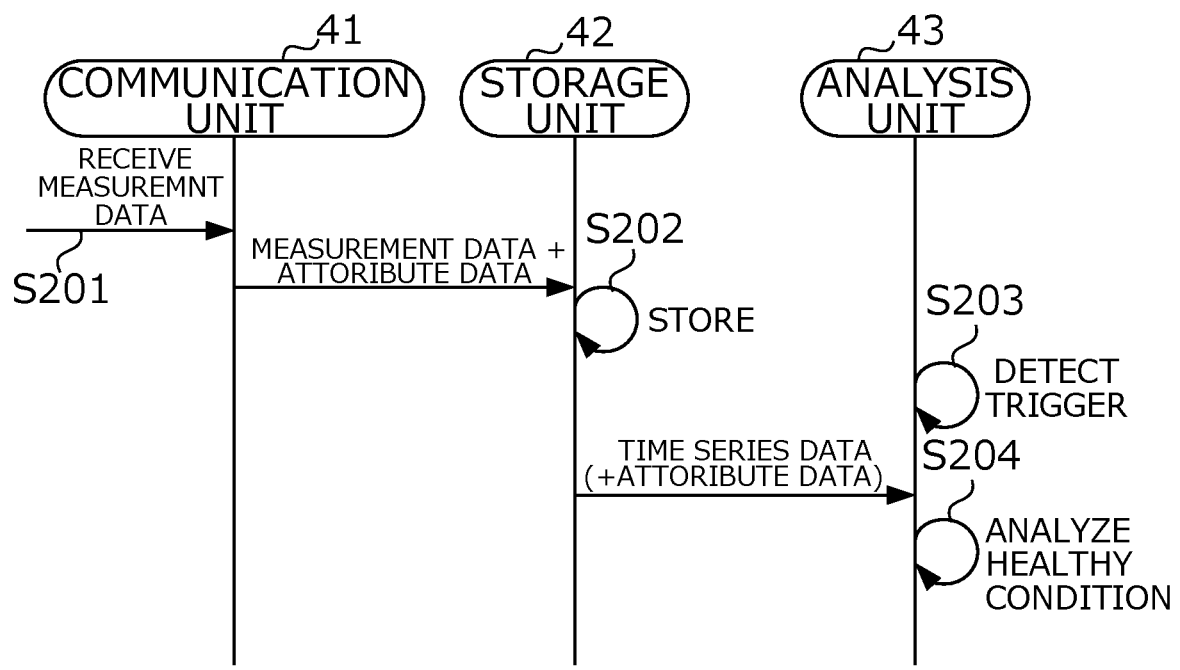
FIG. 17 shows a sequence chart illustrating details of analysis processing.

FIG. 17 shows a sequence chart illustrating details of the analysis process. At step S201, the communication unit 41 of the analysis system 40 receives the measurement data from the user terminal 30. At step S202, the storage unit 42 stores the measurement data and the attribute data. In this example, since the attribute data includes the time stamp and the user identifier, when the measurement data at a plurality of measurement timings is accumulated, the storage unit 42 stores the measurement results of the specific component in the urine in time series. Further, in this example, since the urine sensor 10 measures a plurality of components in the urine, the storage unit 42 stores measurement results of a plurality of specific components in the urine in time series.

Figure 18:
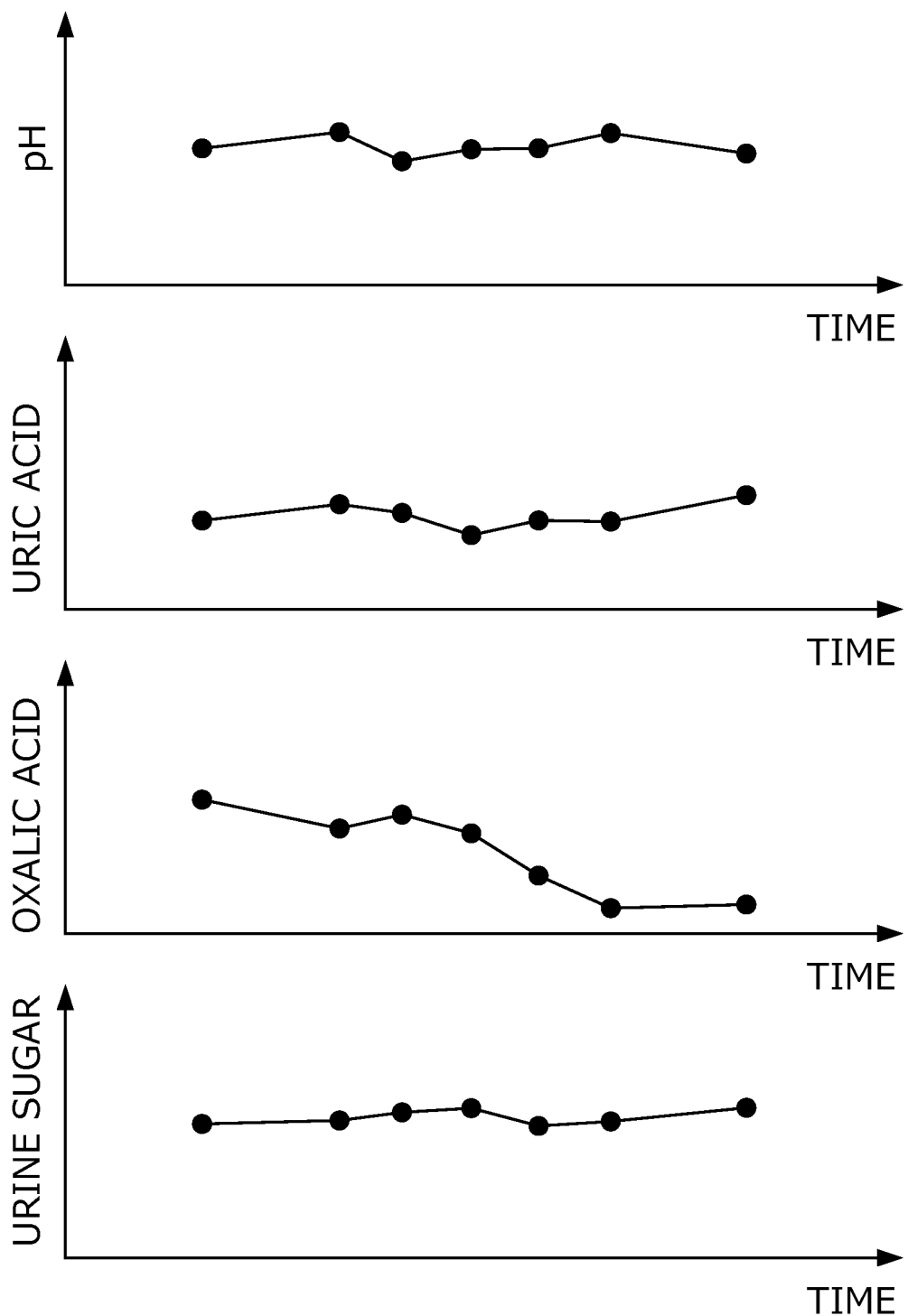
FIG. 18 illustrates a time series of measurement results.

FIG. 18 shows a diagram illustrating a time series of measurement results. In this example, pH, uric acid, oxalic acid, and urinary sugar values are measured in the urine. In the figure, the horizontal axis shows the date and time, and the vertical axis shows the measured values. For example, the user performs measurement using the urine sensor 10 each time urination is performed, and the measurement is performed four times a day on average. According to this example, the time course of the concentration of the four components in the urine is recorded.

Referring to FIG. 17 again. At step S203, the analysis unit 43 detects an event that trigger analysis of a health condition of a user. The event includes a process in which the analysis system 40 receives a user identifier that identifies a user to be analyzed for health status (hereinafter, referred to as a "target user"). This event is, for example, an event in which the user instructs (or notifies the analysis system 40 of) the analysis of the health state in the user terminal 30. Alternatively, the event may be an event in which a new measurement data has been received from the user terminal 30. Further alternatively, the event may be an event in which a predetermined time has elapsed since the previous analysis of the health state of the target user. When the event that triggers the analysis of the healthy condition is measured, the analysis unit 43 shifts the process to step S204.

At step S204, the analyzing unit 43 analyzes the health condition of the target user specified by the user identifiers. Time series data indicating the measurement results of the urine sensor 10 is used for the analysis of the health state. When the urine sensor 10 measures a plurality of components in the urine, the analysis unit 43 refers to the measurement results of the plurality of components to comprehensively determine a health state of the target user.

The components measured by the sensor element 12 are not limited to the above examples. The sensor element 12 measures, for example, at least one of the following components (1) to (12). The following measurement items and their interpretations are merely examples.

(1) pH

If the urine is acidic, the user may have diabetes, cardiovascular disease or alcoholism. When urine is alkaline, the user may have a urinary tract infection or kidney disease.

(2) Uric Acid

High uric acid levels may be associated with gout.

(3) Oxalic Acid

A high oxalate level may indicate ureteral calculi.

(4) Urine Sugar (Glucose)

High levels of urine glucose may be associated with diabetes. However, urine glucose levels vary with diet, and urine must be measured before breakfast.

(5) Protein

Higher levels of protein may be associated with decreased renal function.

(6) Bilirubin

Bilirubin is the bile dye of hemoglobin. High levels of bilirubin may lead to hepatic dysfunction or biliary obstruction.

(7) Urobilinogen

Urobilinogen is the degradation of bilirubin by intestinal bacteria. High levels of urobilinogen may cause damage to the liver or gallbladder.

(8) Specific Gravity

The specific gravity of urine depends on components other than moisture, such as urea or sodium chloride. Low density may result in renal failure, and high density may result in diabetes or dehydration.

(9) Occult Blood

Higher concentrations of occult blood may lead to abnormality in kidneys, ureters, or bladder.

(10) Ketone Body

Ketone bodies are intermediate metabolites during lipolysis. Higher concentrations of ketones may be the result of or lead to diabetes, fever (cold or influenza), or eating disorders.

(11) Nitrite

Nitrate in foods can turn into nitrites. High concentrations of nitrite may cause bladder or urinary tract infections.

(12) Leukocytes

High levels of leukocytes may cause inflammation of the kidneys, bladder, prostate, or seminal vesicles.

2-3. Provision of Information

Figure 19:
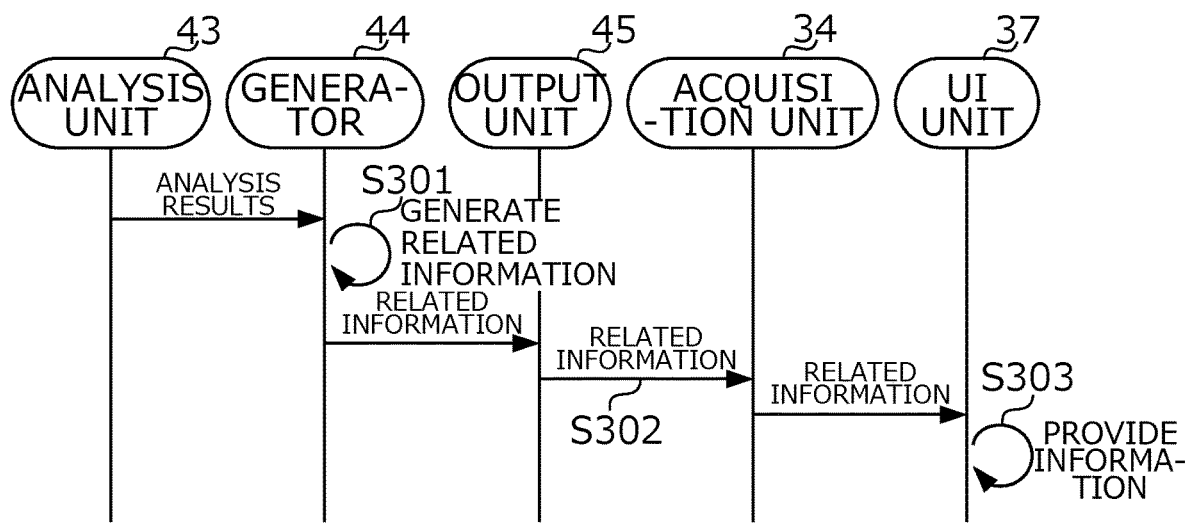
FIG. 19 illustrates details of information provision processing.

FIG. 19 illustrates details of the information providing process. At step S301, the generating unit 44 generates related information corresponding to the analysis results of the healthy state. As the related information, for example, at least one of (1) information directly indicating the analysis results, (2) information obtained by adding an interpretation to the analysis results, (3) advice based on the analysis results, and (4) recommendation of a product related to the analysis results is used; which information provided as the related information is specified by the user, for example. Alternatively, the analysis system 40 may determine which information to provide as the related information according to the analysis results. For example, when the analysis results indicate that there is no particular abnormality in the health state of the target user, the analysis system 40 provides information directly indicating the analysis results (for example, a graph of measurement data) and information obtained by adding interpretation to the analysis results (for example, "no abnormality" display) as related information to the user terminal 30. Alternatively, when the analysis results indicate a new abnormality (an abnormality not previously found) in the health state of the target user, the analysis system 40 provides information directly indicating the analysis results (e.g., a graph of measurement data), information interpreting the analysis results (e.g., suspected disease name), and advice based on the analysis results (e.g., introduction of a hospital where a specialist of the disease is present) to the user terminal 30 as related information. Alternatively, when the analysis results indicate an abnormality that occurs chronically in the health state of the target user, the analysis system 40 provides information (for example, a deficient nutrient) obtained by adding interpretation to the analysis results, and (4) recommendation of a commodity related to the analysis results (introduction of a supplement that can ingest the nutrient) to the user terminal 30 as related information. At step S302, the output unit 45 outputs the related information generated by the generation unit 44 to the user terminal 30 of the target user.

The acquisition unit 34 of the user terminal 30 acquires related information from the analysis system 40. At the step S303, the UI unit 37 provides related information to the user. That is, the UI unit 37 displays an image, a character string, a document, or a web page included in the related information, reproduces a moving image, or outputs sound.

According to the present embodiment, it is possible to easily measure a component in the urine of the user, and furthermore, it is possible to easily provide the user with information according to the measurement results.

3. Other Embodiments

Various modifications of the first embodiment are possible. Several modifications will be described below. Two or more items in the following modifications may be combined.

3-1. Modification 1 (Shape of Transmitter 20)

Figure 20:
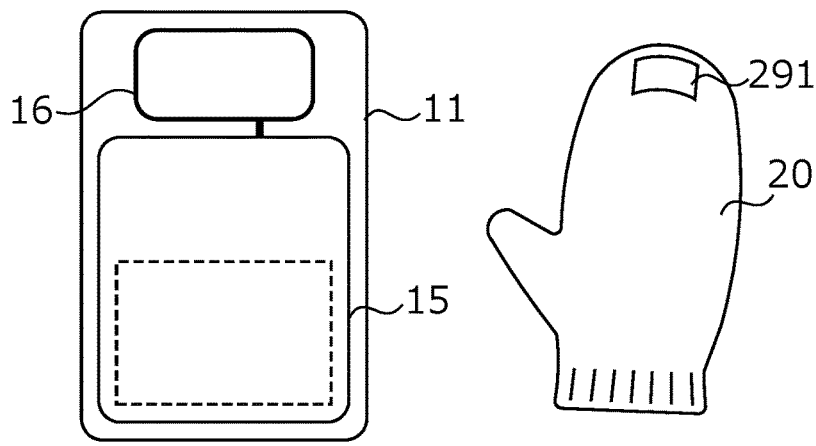
FIG. 20 illustrates another example of a transmitter 20.

FIG. 20 shows another example of the transmitter 20. The shape of the transmitter 20 is not limited to that illustrated in FIG. 9. FIG. 20 shows an example in which the transmitter 20 has the shape of a wearable device, more specifically, a mitten, worn on the user's hand. A wearable device is a device having a shape that can be worn by a user, e.g., a hat, glasses, watch, wristband, glove, shirt, pants, socks, or a device embedded in a shoe. Although not shown in FIG. 20, a hardware element such as a CPU 201 is built in a position corresponding to the back of the hand. In this example, the transmitter 20 does not have a detachment mechanism 29, but instead has an electrode 291. The electrode 291 is an example of a contact for obtaining an electrical connection with the urine sensor 10, and is exposed on the surface of the transmitter 20. The urine sensor 10 corresponding to this transmitter 20 also has, instead of or in addition to the detachment mechanism 13, an electrode 16 for obtaining an electrical connection with the transmitter 20. The electrode 16 is exposed to the base 11. The electrodes 291 and 16 are designed to be positioned, shaped, and sized to contact each other when the user holds the urine sensor 10 with the transmitter 20 (glove) in place.

Upon urination, the user places the transmitter 20 (glove) in his/her hand. The user prepares the urine sensor 10. The user holds the urine sensor 10 with a hand fitted with a transmitter 20. In this state, electrical connection between the urine sensor 10 and the transmitter 20 is established, and an output signal from the urine sensor 10 is transmitted to the user terminal 30. After wiping the urine, the user removes the transmitter 20 and disposes of the urine sensor 10. The transmitter 20 is reused.

3-2. Modification 2 (Signal Transmission)

The transmission path of the signal from the urine sensor 10 to the transmitter 20 is not limited to that through the contact point between the two electrodes. Non-contact signal transmission by electromagnetic induction may be used for transmission of signals from the urine sensor 10 to the transmitter 20. In this case, the transmitter 20 includes a transmission unit (not shown) that performs contactless signal transmission by electromagnetic induction with the urine sensor 10.

Alternatively, the transmitter 20 may be embedded in the base member 11 as a so-called non-contact IC card. In this case, the transmitter 20 does not require a battery, and the circuit of the transmitter 20 operates due to the induced electromotive force obtained by the electromagnetic waves emitted from the reader/writer device. The reader/writer device is built into, for example, the user terminal 30. Alternatively, the reader/writer device may be provided as an external device connected to the user terminal 30. In this case, the transmitter 20 may be non-detachable from the base 11 and may be disposed of as combustible waste with the base 11 or may be flushed down a toilet.

3-3. Modification 3 (Attachment and Detachment Mechanism)

In the urine sensor 10 and the transmitter 20, specific examples of the desorption mechanism 13 and the desorption mechanism 29 are not limited to those exemplified in the embodiment. In the embodiment, an example in which the detachment mechanism 13 and the detachment mechanism 29 are formed by snap fitting has been described. However, the detachment mechanism 13 and the detachment mechanism 29 may be formed from a surface fastener that uses a conductive material.

3-4. Modification 4 (Data)

The data output from the user terminal 30 to the analysis system 40 is not limited to the measurement data. Data other than the measurement data may be output to the analysis system 40 as long as the information is used to determine a health condition of the user. The other data is, for example, data including information on food and drink consumed by the user (hereinafter referred to as "food and drink data"). The information on the food and drink is, for example, information specifying a time when the food and drink was ingested, a name of the ingested food and drink, and an amount of the ingested food and drink. Alternatively, the other data may be data that includes information relating to exercise performed by the user; for example, information specifying an intensity of the exercise and a time period of the exercise. Still alternatively, the other information may include attributes of the user, such as age, sex, and medical history. When these data are provided, the analysis system 40 analyzes the health condition of the user by taking into account these data in addition to the measurement data. That is, the generating unit 44 generates the related information according to the measurement data and the food and drink data.

The food and drink data may include, for example, a photograph of a meal. When the user takes a meal, the user takes a photograph of the meal with the user terminal 30. The user terminal 30 includes a camera (not shown) for taking pictures. The user terminal 30 outputs the photograph of the dish, which constitutes the meal, to the analysis system 40. The photograph time stamped, and the time stamp is used to obtain the time of consumption of the meal. The analysis system 40 accesses the AI for analyzing the photograph of the meal to determine calories and nutrients, and acquires information indicating the calories and nutrients of the meal consumed by the user.

In one example, the health supplement system 1 may be used to demonstrate an effect of a functional food or health supplement (hereinafter referred to as "health food"). For example, juices of certain green vegetables are known to have the effect of rendering the body alkaline. According to the health support system 1 of the present embodiment, the effects of these health foods can be verified.

Figure 21:
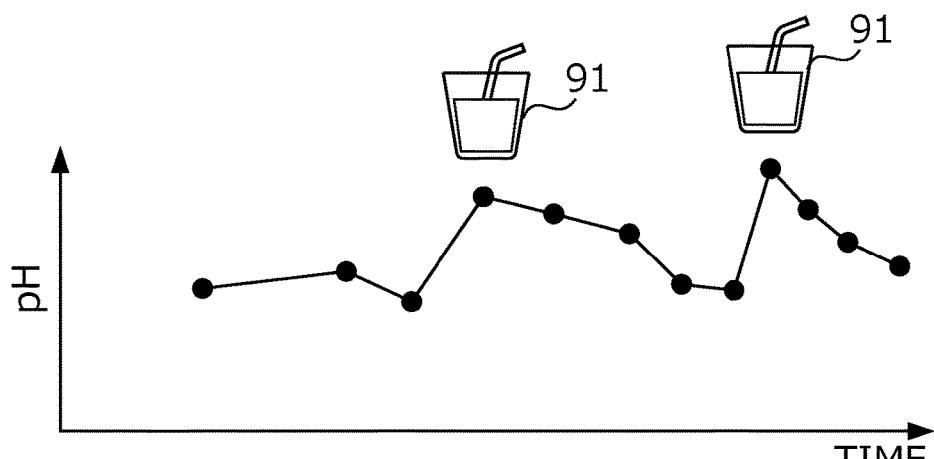
FIG. 21 illustrates demonstration of the effectiveness of health foods.

FIG. 21 illustrates a demonstration of the effect of a health food. FIG. 21 illustrates an example of a UI screen in the user terminal 30. This screen contains a graph showing a time course of ingredients (e.g., pH) associated with the health food. In addition, a time of ingestion of the health food is shown in the graph. In this example, an icon 91 is shown at a position corresponding to a time when the user ingested the health food. In the example shown, the urine changes to alkaline immediately after ingestion of the health food, and then gradually changes to acidic. According to this example, it is possible to visually represent the effect of the ingestion of the health food. This system can improve the user's motivation to maintain health and prevent illness, as well as to promote the sale of health foods.

3-5. Modification 5 (for Common Use of Transmitters)

In an embodiment, one transmitter 20 is dedicated to a particular user. However, one transmitter 20 may be shared by a plurality of users. In this case, the transmitter 20 has a plurality of storage areas corresponding to different identifiers or users. That is, each storage area is set to a separate identifier. One identifier is used by one user. For example, when the storage unit 23 has four identifiers (four storage areas), the transmitter 20 can be shared by a maximum of four users. In this example, the transmitter 20 further includes a receiving unit (not shown). The receiving unit receives one of a plurality of identifiers. The receiving unit is a type of UI element, and is, for example, a switch. The storage unit 23 stores the measurement data in the storage area corresponding to one identifier designated through the reception unit among the plurality of storage areas. The wireless communication unit 24 transmits the data stored in the storage area corresponding to the one identifier specified via the receiving unit and the wireless signal indicating the one identifier. For example, when the four users have their own user terminals 30, the transmitter 20 establishes a connection with the user terminal 30 corresponding to the user specified by the receiving unit from among the four user terminals 30.

In the case where one transmitter 20 is shared by a plurality of users, the transmitter 20 may not have a plurality of storage areas corresponding to the plurality of users. In this case, for example, the user terminal 30 is shared by a plurality of users. The user terminal 30 switches the user by a so-called login process. The user terminal 30 adds the user identifier of the logged-in user to the measurement data.

3-6. Modification 6 (Encryption)

The transmitter 20 may encrypt the measurement data when transmitting the measurement data to the user terminal 30. In this case, the transmitter 20 and the user terminal 30 exchange the encryption key prior to transmission and reception of the measurement data. In one example, the user terminal 30 transmits an encryption key to the transmitter 20. The transmitter 20 encrypts the data using the encryption key and then transmits the measurement data to the user terminal 30. The user terminal 30 decrypts the measurement data using the encryption key transmitted to the transmitter 20 and the corresponding decryption key. Since such measurement data constitutes personal information, there is a security risk if the data is transmitted as plain text, but the security risk can be reduced by use of encryption.

3-7. Modification 7 (Convergence Condition)

The convergence conditions for determining that the measured value obtained from the urine sensor 10 has converged are not limited to those exemplified in the embodiment. For example, the provider of the urine sensor 10 confirms the time τ until the measured value converges in the urine sensor 10 in advance by an experiment. The provider of the urine sensor 10 sets the value of the time τ in the client program. The control unit 36 of the user terminal 30, when the elapsed time from the time when the measurement value begins to be obtained (e.g., time t2 in FIG. 14) exceeds τ, the measured value may be determined to have converged. Alternatively, the user terminal 30 may output the measurement data to the analysis system 40 at predetermined time intervals after the time when the measurement value starts to be obtained without determining whether the measurement value has converged, and the analysis system 40 may determine whether the measurement value has converged. If it is determined that the measured value has converged, the analysis system 40 notifies the user terminal 30 of the convergence. Upon receiving this notification, the user terminal 30 stops outputting the measurement data.

3-8. Modification 8 (Time Division Processing)

The output signal from the plurality of sensor elements 12 in the embodiment has been described as an example in which the transmitter 20 wirelessly transmits to the user terminal 30 in time division. Even if the urine sensor 10 has a plurality of sensor elements 12, the transmitter 20 may not transmit the output signals from all of the sensor elements 12 in a time division manner. For example, among the plurality of sensor elements 12 the transmitter 20 may, output only the output signal from the sensor element 12 of a portion selected by the user (e.g., one). In this case, the transmitter 20 may have a UI element (e.g., a switch) for selecting the sensor element 12 of interest. Alternatively, the user may select the target sensor element 12 at the user terminal 30 and the user terminal 30 may transmit information to the transmitter 20 identifying the target sensor element 12. From among the plurality of sensor elements 12, the transmitter 20 outputs only the output signal of a portion of the sensor element 12 selected by the user in time division (when a single sensor element 12 is selected outputs only the output signal of the sensor element 12 without time division).

In another example, the urine sensor 10, rather than the transmitter 20, may have time-sharing processing capabilities. In this case, the urine sensor 10 has a circuit corresponding to the selector circuit 222. The urine sensor 10 outputs a signal in which the output signals from the plurality of sensor elements 12 are time-division multiplexed to the transmitter 20. According to this example, a number of output terminals and input terminals for transmitting signals from the urine sensor 10 to the transmitter 20 can be reduced.

3-9. Modification 9 (Combination of Measurement Items)

A provider of urine sensors 10 may combine different types of sensor elements 12 in providing a urine sensor 10 having a plurality of sensor elements 12. For example, in providing a urine sensor 10 having four sensor elements 12, in one product (hereinafter referred to as urine sensor 10A), sensor elements 12A-D may measure pH, uric acid, oxalic acid, and urine sugar; and in another product (hereinafter referred to as urine sensor 10B), sensor elements 12A-D may measure specific gravity, occult blood, ketone bodies, and nitrite. The provider of the urine sensor 10 assigns an identification code to the combination of the sensor elements 12. The identification code may be, for example, a string (e.g., an identification number) or an image (e.g., a so-called two-dimensional bar code). This identification code is provided, for example, on the surface of the base 11 or in the package of the urine sensor 10. The user enters an identification code, e.g., as provided on the base 11 or package, into the user terminal 30. The user terminal 30 has information for converting the identification code into a combination of measurement items, for example, acquired from the analysis system 40, and refers to this information to determine which sensor element 12 output signal indicates which measurement item results. According to this example, it is possible to provide a urine sensor 10 having various combinations of measurement items.

3-10. Modification 10 (Sharing of Processing)

The sharing of processing in each device is not limited to those described in the embodiments. For example, at least a portion of the processing performed in the analysis system 40 in the embodiment may be performed by the user terminal 30. As an example, the storage unit 31 of the user terminal 30 may store the measurement data in time series. The control unit 36 generates time-series data using the time-series measurement data stored in the storage unit 31, or the control unit 36 performs statistical processing on the time-series measurement data to generate statistically processed measurement data. The user terminal 30 outputs the generated data to the analysis system 40.

In another example, even when the user terminal 30 outputs the measurement data to the analysis system 40, the storage unit 31 of the user terminal 30 may store the same data as that output to the analysis system 40. In particular, when the analysis system 40 is implemented in a cloud computing system, if the measurement data is stored in the storage unit 31, some processing such as confirmation of measurement data and statistical processing can be performed locally (without connecting to a network).

3-11. Modification 11 (Shape of Base)

The shape and material of the base 11 are not limited to those illustrated in the embodiments. For example, the base 11 may be a diaper worn by a subject.

3-12. Other Variations

The present invention is not limited to the embodiments described above, and various modifications can be made. Several variations are described below. The following modifications are applicable to the embodiments described above. In addition, two or more of the following modified examples may be applied in combination. Further, at least a portion of each of the embodiments and variations may be combined with at least a portion of other embodiments and variations.

Although an example in which urine is measured has been described in the above embodiment, the subject of measurement is not limited to urine. The health supporting system according to the present invention may measure body fluids other than urine, such as sweat, saliva, or blood.

The specific hardware configuration of each element constituting the health support system according to the above embodiment is not limited to that exemplified in the embodiment. Each element may have any appropriate hardware configuration.

What is claimed is:

1. A health support system, comprising:
    a sensor that outputs an output signal corresponding to a specific component in urine;
    a transmitter connected to the sensor;
    a user terminal held by the user,
    wherein the transmitter includes,
        an input unit into which the output signal of the sensor is input,
        a storage unit that stores an identifier of the transmitter,
        a radio communicator that transmits a radio signal indicating data corresponding to the output signal and the identifier
    the user terminal includes
        a storage unit that stores an identifier corresponding to the user,
        a wireless receiver that receives the radio signal from the transmitter,
        an output unit that outputs the data to an analysis system that analyzes a health condition of the user based on the specific component indicated by the data when the identifier indicated by the radio signal matches the identifier stored in the storage unit,
        an acquiring unit that acquires information corresponding to the results of the analysis from the analysis system.

2. The health support system according to claim 1, wherein
    the sensor includes
        a base,
        a sensor element attached to the base, and
        a detachable mechanism that detachably fixes the transmitter and includes a transmission path of the output signal of the sensor.

3. The health support system according to claim 2, wherein
    the sensor includes a sheet covering the sensor element,
    the base is made of a combustible material having a planar shape, and
    the sheet is made of paper softer than the base.

4. The health support system according to claim 3, wherein
    the sheet includes a thinner area than other areas, and
    the thinner area covers the sensor element with the sheet attached to the base.

5. The health support system according to claim 3, wherein
    the sheet includes a pocket, and
    the sensor element is housed in the pocket.

6. The health support system according to claim 3, wherein
    the base includes an adhesive layer for folding the base on the surface to which the sensor element is attached.

7. The health support system according to claim 6, wherein
    a protective film is adhered to the sheet at a position covering the adhesive layer on a surface of the sheet facing the base,
    when the sheet is attached to the base, the adhesive layer is not exposed, and
    when the sheet is peeled off from the base, the adhesive layer is exposed.

8. The health support system according to claim 2, wherein
    the base is an undergarment or a diaper worn by a subject.

9. The health support system according to claim 2, wherein
    the sensor element includes
        a first sensor element that measures a first component in the urine,
        a second sensor element that measures a second component in the urine different from the first component.

10. The health support system according to claim 9, wherein
    the transmitter includes
        a first terminal into which the output signal of the first sensor element is input,
        a second terminal into which the output signal of the second sensor element is input, and
        a processor that processes in time division the signal input through the first terminal and the signal input through the second terminal.

11. The health support system according to claim 9, wherein
    the sensor includes
        a selector circuit that selects in time division the output signal of the second sensor element or of the first sensor element,
        an output terminal that outputs a signal showing the output signal of the first sensor element and the second sensor element selected in time division by the selector circuit.

12. The health support system according to claim 1, wherein
    the transmitter is a wearable device worn on the user's body.

13. The health support system according to claim 12, wherein
    the wearable device includes an exposed contact on electrodes for obtaining electrical connections with the sensors.

14. The health support system according to claim 12, wherein
    the wearable device includes a transmission unit that performs non-contact signal transmission by electromagnetic induction with the sensor.

15. The health support system according to claim 1, wherein
    the storage unit includes a plurality of storage areas corresponding to each different identifier,
    the transmitter includes a receiving unit that receives designation of any of the plurality of storage areas,
    the storage unit stores data indicated by the output signal in one of the plurality of storage areas designated via the receiving unit, and
    the wireless communication unit transmits the wireless signal indicating the data stored in the designated one storage area and the identifier corresponding to the one storage area.

16. The health support system according to claim 1, further comprising:
    the analysis system, wherein
    the analysis system includes
        a storage unit that stores time series data indicating measurement results of the specific components in time series for each of a plurality of users, a generating unit that generates information related to the measurement results for the target user from among the plurality of users, using the time series data of the user, and an output unit that outputs the related information to a user terminal corresponding to the user.

17. The health support system according to claim 16, wherein the user terminal includes a receiving unit that receives input of information specifying food and drink consumed by the user, and the output unit outputs information on food and drink consumed by the user.

18. The health support system according to claim 17, wherein the generating unit generates the related information in accordance with the information about the food and drink, and the data.

19. The health support system according to claim 18, wherein the generating unit generates, as the related information, an image indicating a temporal change of a specific component in urine and a timing of ingestion of the food and drink.

20. The health support system according to claim 1, wherein the transmitter includes a power supply function to the sensor.

21. A health support method using a health support system having a sensor that outputs an output signal corresponding to a specific component in urine, a transmitter connected to the sensor, and a user terminal carried by the user, the method comprising:

transmitting, by the transmitter, data responsive to an output signal of the sensor and a radio signal indicative of the identifier of the transmitter;

receiving, by the user terminal, the radio signal from the transmitter, outputting, by the user terminal, the data to an analysis system that analyzes the health condition of the user based on the specific component indicated by the data if the identifier indicated by the radio signal matches the identifier corresponding to the user obtaining information corresponding to the results of the analysis from the analysis system.

22. A sensor comprising:

a base;

a first wiring provided on the base;

a second wiring provided on the base;

a sensor element that outputs an output signal corresponding to a specific component in urine, the sensor element being connected to the first wiring and the second wiring, and a detachable mechanism connected to the first wiring and the second wiring, having a transmission path of an output signal transmitted through the first wiring and the second wiring, the detachable mechanism detachably fixing the transmitter that wirelessly transmits data indicating the output signal to another device.

23. The sensor according to claim 22, wherein the base is an undergarment or a diaper worn by a subject.

* * * * *